United States Patent [19]

Tretbar

[11] Patent Number: 4,671,282

[45] Date of Patent: Jun. 9, 1987

[54] CLIP APPARATUS

[76] Inventor: Lawrence L. Tretbar, 8901 W. 74th St., Shawnee Mission, Kans. 66204

[21] Appl. No.: 784,529

[22] Filed: Oct. 4, 1985

[51] Int. Cl.$^4$ .............................................. A61B 17/00
[52] U.S. Cl. .................................. 128/346; 128/325; 128/321; 24/703
[58] Field of Search ............... 128/325, 326, 346, 337, 128/321; 24/115 A, 703, 456

[56] References Cited

U.S. PATENT DOCUMENTS

| | | |
|---|---|---|
| 2,294,852 | 9/1942 | Smith . |
| 2,595,462 | 5/1952 | Johnson . |
| 3,032,039 | 5/1962 | Beaty .................................. 128/326 |
| 3,166,819 | 1/1965 | Robbins . |
| 3,270,745 | 9/1966 | Wood .............................. 24/115 A |
| 3,760,811 | 9/1973 | Andrew . |
| 3,802,437 | 4/1974 | Kees ................................... 128/325 |
| 3,814,080 | 6/1974 | Norman . |
| 4,398,907 | 8/1983 | Crais . |
| 4,484,911 | 11/1984 | Berlin et al. . |
| 4,491,136 | 1/1985 | LeVeen . |

OTHER PUBLICATIONS

Ligaclip, copy of label sold by Ethican.
"A Simple Method for Catheter Fixation of the Cystic Duct During Cholangiography" by Hampson et al.

Primary Examiner—Michael H. Thaler
Attorney, Agent, or Firm—Litman, Day & McMahon

[57] ABSTRACT

A clip apparatus for use in cholangiography or the like includes a clip, a catheter and a tool for applying and removing the clip from the cystic duct or the like. The clip preferably has two opposed C-shaped surfaces in jaws which can be biased together such that opposed edges touch to apply the clip or spread apart such that at least one set of opposed edges is spread to allow removal of the clip. The clip includes arms attached to the jaws which are medially bent outward at the time the clip is applied and which are compressible to rotate the jaws relative to one another about a common fulcrum to space sides of the jaws opposite the fulcrum and allow easy removal of the clip. The catheter is inserted in the cystic duct during a cholangiography procedure and held therein by the clip. The catheter is serrated on the surface thereof which engages the duct beneath the clip.

4 Claims, 8 Drawing Figures

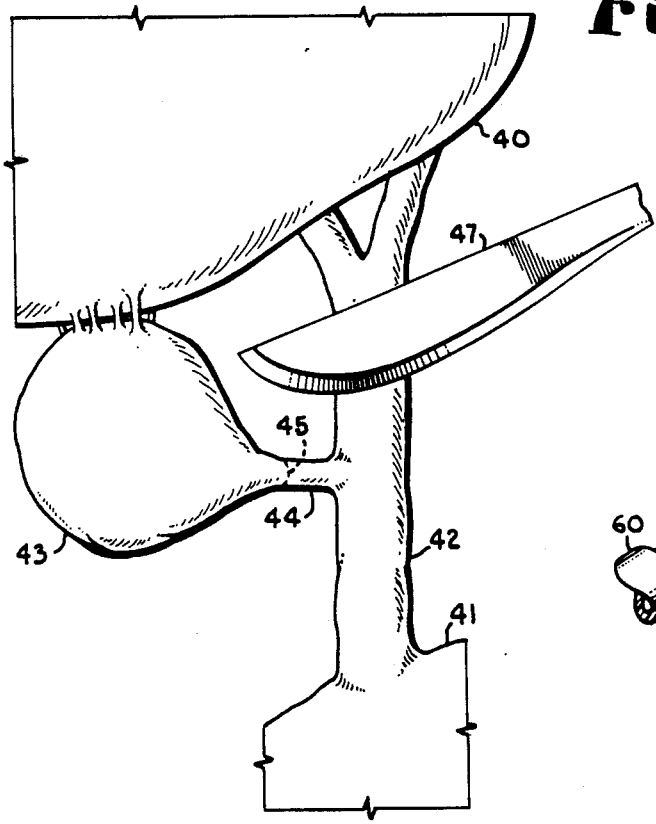
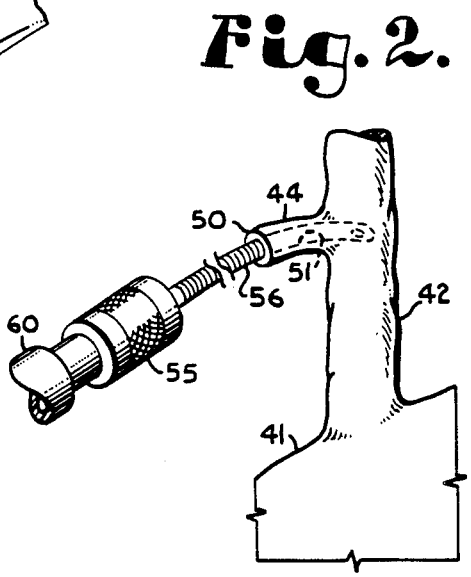
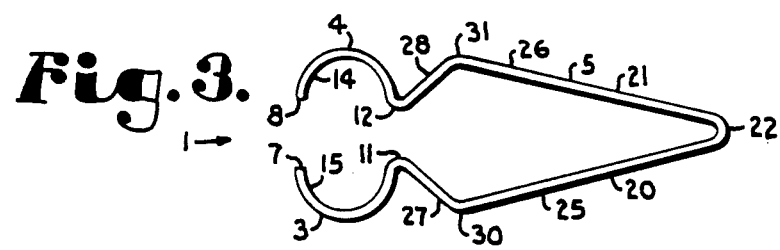
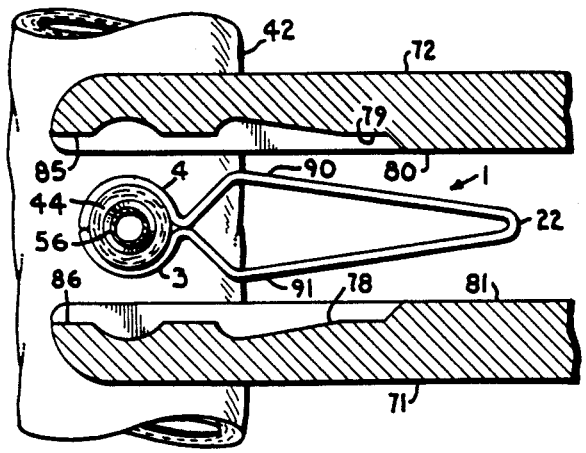

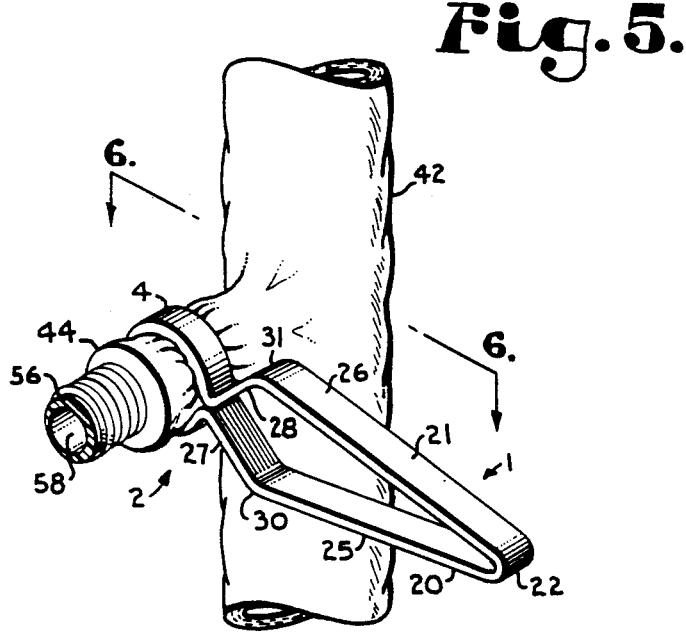
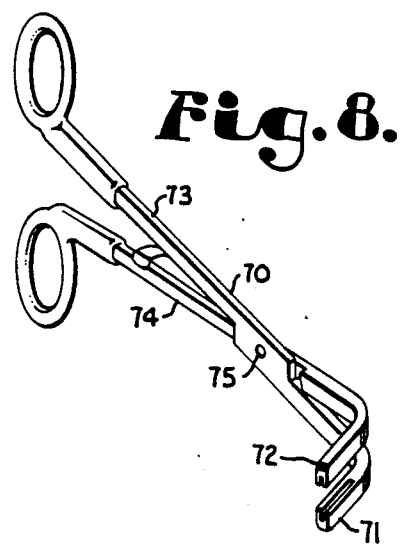
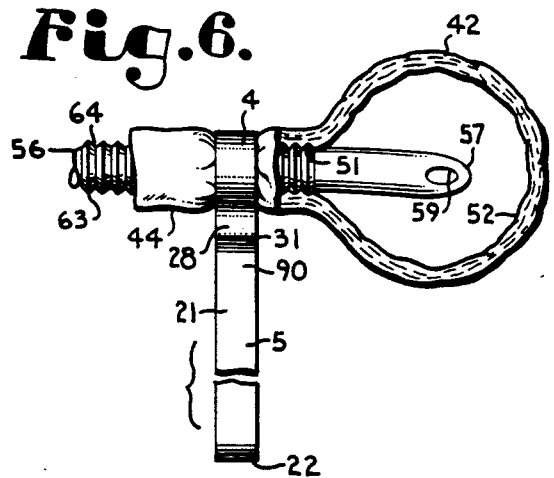
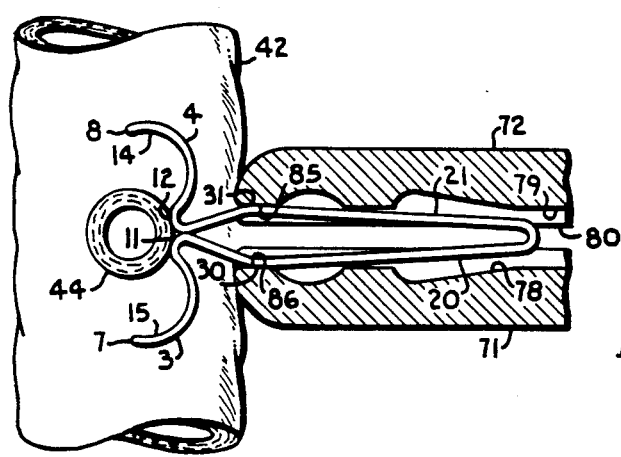

CLIP APPARATUS

BACKGROUND OF THE INVENTION

This invention relates to a clip apparatus and, in particular, to a clip apparatus utilized in cholangiography and similar procedures wherein a catheter or the like is placed in a duct or vessel and held therein by a clamp mechanism.

Many medical procedures require that a catheter, tube or the like be placed in a body duct or vessel and held therein while some medical procedure is performed. For example, plastic catheters are often placed in veins and held therein by a stitch or by a loop of string tied around the catheter. Similarly, a tubular structure must be held within a vessel during a lymphangiogram or in an IV cut down procedure. During cholangiography, a cannula must be sealably held within the cystic duct.

In humans, the common bile duct joins the liver with the duodenum to provide flow of bile from the liver to the small intestine to assist in the digestion of fats. The gallbladder is a sac-like structure which communicates with the common bile duct through the cystic duct and provides intermittent storage for excess bile produced by the liver, especially between meals. Gallstones sometimes occur in the bile and block or impede flow of the bile through the various ducts. When this occurs, the gallbladder may have to be surgically removed (cholecystectomy).

To ensure removal of all gallstones from the common bile duct, cholangiography is normally perfomed on the ductile system of the biliary tract which comprises the injection of a radiopaque dye into the duct followed by a series of x-rays. The x-rays tend to image the outlines of any stones or obstructions within the ducts, as variances in opacity occur where the stones prevent the dye from filling the duct.

Normally, the dye is injected into the common bile duct through a relatively small catheter which is inserted into a severed end of the cystic duct. It is important to form a relatively tight fluid seal between the cystic duct and the catheter. Such a seal prevents the dye from leaking out of the cystic duct rather than passing through the common bile duct to image the gallstones therein.

In order to produce such a tight seal, surgeons initially utilized a suture which was tied securely around the cystic duct to hold the catheter in place. Because it is difficult and cumbersome to tie the suture at this location, many surgeons have elected to utilize a commercially available metallic hemoclip for this purpose. The hemoclips were designed to have opposing walls which flatten against one another to flatten a severed blood vessel or the like to prevent leakage therefrom. As this type of clip was designed to compress flatly and not in a circle, there is a tendency for the tissue of the cystic duct to ovate when the clip is applied so that leakage occurs between the cystic duct and the catheter on the sides of the duct not compressed by the clip. In addition, the clip must be pried loose to remove.

Some complex mechanical clips have also been designed to be used for this purpose. However, such clips tend to be cumbersome as well as relatively expensive.

Hence, it was desired to produce a relatively simple clip which could be easily and quickly applied to the cystic duct which would compress the cystic duct fairly evenly about its entire circumference and which would be fairly easily removed after completion of the cholangiograpic process.

In addition, it was desired to have a catheter which would cooperate with the clip to provide a leak-proof seal. Further, it was desired to provide a tool which would both readily apply and remove the clip, as well as a process for utilization of the clip during surgical procedures.

OBJECTS OF THE INVENTION

Therefore, the objects of the present invention are: to provide a clip apparatus which includes a medical clip providing a relatively fluid-type seal between a vessel and a tube within the vessel when the clip is cooperatively placed around the vessel; to provide such a clip which compresses the vessel relatively evenly about the entire circumference of the vessel; to provide such a clip which is relatively easy to apply and simple in nature; to provide such a clip which is relatively easy to remove; to provide such a clip which is especially well adapted for use in compression of the cystic duct about a catheter during cholangiography; to provide such a clip which includes a pair of opposed C-shaped jaws interconnected by arms at a semimaleable juncture which allows selective positioning of the jaws when pressure is applied to the arms and/or jaws; to provide such a clip wherein the arms may be partially urged toward one another to compress the jaws and wherein the arms can be further compressed in such a manner as to urge the jaws apart to facilitate removal of the clips; to provide such an apparatus including a catheter having serrations thereon for cooperating with the clip to form a fluid-type seal between the catheter and the duct; to provide such an apparatus including an application and removal tool for the clip; to provide a process for utilization of the clip during a cholangiographic process or the like; to provide such a clip apparatus which is relatively simple and inexpensive to make, simple to use and particularly well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a fragmentary view of internal organs of a human including liver, gallbladder, common bile duct and duodenum shortly prior to severing of the cystic duct connecting the gallbladder with the common bile duct with a surgical instrument.

FIG. 2 shows insertion of a cholangiographic process catheter into the cystic duct after the gallbladder is severed therefrom.

FIG. 3 is a side elevational view of a clip according to the present invention.

FIG. 4 is a side elevational view of the clip in a closed position just subsequent to applying the clip to the cystic duct by utilization of a clip applying tool.

FIG. 5 is an enlarged and fragmentary perspective view of the common bile duct and cystic duct with the catheter placed within the cystic duct and held therein by the clip.

FIG. 6 is a fragmentary and enlarged cross-sectional view of the common bile duct and cystic duct with the catheter positioned within the cystic duct and held therein by the clip, taken along line 6—6 of FIG. 5.

FIG. 7 is a fragmentary and enlarged side elevational view of the common bile duct and cystic duct showing the clip in an open position after removal from the cystic duct and showing the clip applying tool being utilized to remove the clip.

FIG. 8 is a perspective view on a smaller scale of the clip applying tool.

DETAILED DESCRIPTION OF THE INVENTION

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a clip included in a clip apparatus 2 in accordance with the present invention. The clip 1 comprises a pair of opposed C-shaped jaws 3 and 4 interconnected by a handle 5. Although the clip 1 is shown utilized in conjunction with a cholangiographic process as described below, it is foreseen that the clip 1 may be utilized in other medical procedures requiring the sealing of a vessel or duct about a circular tube or the like.

As seen in FIG. 3, the jaws 3 and 4 are spaced from one another prior to use. The jaws 3 and 4 each have distal ends 7 and 8 respectively which are spaced opposite one another. The jaws 3 and 4 also have fulcrum ends 11 and 12 respectively which are also spaced opposite one another prior to use of the clip 1. The ends 11 and 12 are directly attached to the handle 5. The jaws 3 and 4 have facing surfaces 14 and 15 which are generally semicircular in cross-section and concave. In certain procedures where the clip is to be positioned on the vessel for a relatively long time, the jaw surface may be slightly parabolic rather than semicircular to allow blood to flow from one side of the clip to the other.

The handle 5 includes arms 20 and 21 joined at a semimaleable but not springy hinge 22. The hinge 22 and, preferably, the entire clip 1 is constructed of a generally nonresiliant but semimaleable material which may be bent or manipulated into a modified position when pressure or force is applied thereto, but which substantially retains the modified position when the force is removed. Therefore, if force is applied to the arms 20 and 21 to swing the arms relative to one another about the hinge 22 and change the angle thereof with respect to one another, the arms 20 and 21 will retain the new angular relationship between each other after the pressure is removed.

Each of the arms 20 and 21 include a first portion 25 and 26 and a second portion 27 and 28 respectively. The arm first portions 25 and 26 are relatively straight and join at the hinge 22. The arm second portions 27 and 28 are also relativley straight and join at one end thereof with the arm first portions 25 and 26 respectively opposite the hinge 22 and at the other end thereof with the jaw fulcrum ends 11 and 12 respectively.

Prior to use, the arms 20 and 21 are not linear between the jaw fulcrum ends 11 and 12 respectively and the hinge 22, but rather bow outwardly from one another. In particular, the arm portions 25 and 27 meet at juncture 30 and the arm portions 26 and 28 meet at juncture 31 such that junctures 30 and 31 are spaced substantially outward from linear projections between the hinge 22 and the jaw fulcrum ends 11 and 12 respectively.

The clip 1 has a first configuration which is shown in FIG. 3 and corresponds to the clip 1 prior to use thereof. The clip 1 has a second configuration shown in FIG. 4 which corresponds to the configuration of the clip 1 during use thereof. The clip 1 has a third configuration which is shown in FIG. 7 and which corresponds to the configuration of the clip 1 subsequent to removal thereof following use. These three configurations will be discussed in greater detail below.

FIG. 1 shows part of the internal organs of a human. In particular, a liver 40 is shown interconnected with a duodenum 41 by a common bile duct 42. The bile duct 42 is further connected to a gallbladder 43 by a cystic duct 44. The gallbladder 43 is about to be severed from the cystic duct 44 along an imaginary cut line 45 by a surgical instrument 47. FIG. 2 shows the common bile duct 42 and cystic duct 44 subsequent to severing of the gallbladder 43 from the cystic duct 44. The cystic duct has a free and open end 50 communicating with an internal lumen 51 thereof. The common bile duct 42 also has an internal lumen 52, as can be seen in FIG. 6.

Also in FIG. 2, the clip apparatus includes an instrument 55 for injecting a radiopaque dye into the common bile duct 42. The instrument 55 comprises a catheter 56 having a tip 57, an internal lumen 58 and an aperture 59 near the tip 57 opening into the lumen 58. The instrument 55 further includes a syringe 60 connected to the catheter 56 by a Luer Lock or the like and partially seen in FIG. 2. The syringe 60 holds dye and allows an operator to urge dye into and through the catheter 56. The catheter 56 is corrugated so as to have a plurality of ridges or serrations 63 generally equally spaced along a substantial portion of an outer surface 64 thereof.

As seen in FIG. 8 and partially in FIGS. 4 and 7, the clip apparatus 2 further includes a tool 70 having opposed jaws 71 and 72, arms 73 and 74 joined with said jaws 71 and 72 respectively and a hinge or pivotal connection 75 positioned medially along the arms 73 and 74. The arms 73 and 74 are fixedly attached to the jaws 71 and 72 respectively such that the jaws 71 and 72 extend at right angles to the arms 73 and 74. The arms 73 and 74 are joined by the pivotal connection so as to form a pliers-like tool wherein movement of the distal ends of the arms 73 and 74, opposite the jaws 71 and 72, together urges the jaws 71 and 72 together whereas outward movement of the distal ends of the arms 73 and 74 relative to one another separates or spaces the jaws 71 and 72.

The tool jaws 72 and 73 have recesses 78 and 79 respectively positioned on facing surfaces 80 and 81 thereof. The recesses 78 and 79 are shaped to roughly conform with outer surfaces 90 and 91 of a nonused clip 1.

In FIG. 4, the jaws 71 and 72 are spaced from the clip 1, but positioned such that the recesses 78 and 79 are generally aligned to mate with the outer surfaces 90 and 91 of the clip 1. The tool jaws 71 and 72, as shown in FIG. 4, have just released the clip 1 after compressing the C-shaped jaws 3 and 4 of the clip 1 together so that jaw distal ends 7 and 8 touch and jaw fulcrum ends 11 and 12 touch. During such compression, the clip arm first portion 25 and second portion 27 as well as the clip arm first portion 26 and second portion 28 remain substantially unchanged and generally retain the same angle therebetween. Each of the jaws 71 and 72 have a face forward portion 85 and 86 respectively which are generally parallel and do not align with any particular structure of the clip 1 when the clip 1 is being installed by the tool 70.

The surfaces 85 and 86 however can be aligned to be positioned in opposed relationship to each other over the junctures 30 and 31 of the arms 20 and 21 respectively, as seen in FIG. 7. Upon movement of the jaws 71 and 72 together, the junctures 30 and 31, which are V-shaped, are pressed toward each other so as to make a wider V, that is, to change the relative angle between the first portions 25 and 26 and second portions 27 and 28 of the arms 20 and 21 respectively so as to make the arms 20 and 21 closer to being linear. Such modifications of the arms 20 and 21 rotate the clip jaws 3 and 4 about their fulcrum ends 11 and 12 so that the jaw distal ends 7 and 8 substantially separate, as is shown in FIG. 7. The clip 1 is then in the open configuration thereof and easily removed from the cystic duct 44.

It is also foreseen that only one of the arms of the clip could be bent in order for the clip to open as described above; however, only one of the jaws would rotate about the fulcrum point.

Therefore, in use, the clip 1 is illustrated in conjunction with a cholangiography process. In particular, the cystic duct 44 is severed and the catheter 56 is inserted into the cystic duct lumen 51 such that the catheter tip 57 extends into the common bile duct lumen 52. The clip 1 is originally in the first configuration shown in FIG. 3 wherein the C-shaped jaws 3 and 4 are spaced on both sides.

The clip 1 is positioned within the tool 70 such that the outer surfaces 90 and 91 of the clip 1 mate with the recesses 78 and 79 of the tool. The clip 1 is then positioned such that the C-shaped jaws 3 and 4 are placed on opposite sides of the cystic duct 44 at a location whereat the catheter 56 is passing through the cystic duct 44 with at least several of the ridges 63 positioned beneath the clip surfaces 13 and 14. The distal ends of the tool arm 73 and 74 are urged together by manual pressure thereby urging the tool jaws 71 and 72 together and subsequently urging the clip C-shaped jaws 3 and 4 together such that jaw ends 7 and 8 touch and jaw ends 11 and 12 touch as seen in FIG. 4. The hinge 22 is maleable so that the arms 20 and 21 may be bent about the hinge 22 and fold the portion they are bent to without requiring additional biasing such as springs or the like. The tool 70 is then removed from the clip 1 as shown in FIG. 4. Dye is then injected through the catheter 56 to perform a cholangiographic process. The clip 1 is sized such that the surfaces 13 and 14 form tightly about the cystic duct 44 and the catheter 56 to form a tight fluid neck therebetween.

After the dye is injected, the tool jaws 71 and 72 are then placed on the clip junctures 30 and 31 and again pressure is exerted on the tool jaws 71 and 72 by manipulation of the tool arms 73 and 74. The clip junctures 30 and 31 are urged together bending the arms 20 and 21 to be more linear which rotates the clip C-shaped jaws 3 and 4 about their respective fulcrum ends 11 and 12 such that the distal ends 7 and 8 thereof substantially separate, thereby presenting a third or used-open configuration of the clip, as seen in FIG. 7. The clip 1 is then removed from the cystic duct 44 as is the catheter 56. Normally, a sealing clip (not shown) is thereafter placed on the cystic duct 44 near the common bile duct 42 and the excess cystic duct stub extending away from the clip is surgically removed.

It is to be understood that while certain forms of the present invention have been illustrated and described herein, it is not to be limited to the specific forms or arrangement of parts described and shown.

What is claimed and desired to be secured by Letters Patent is as follows:

1. A medical clip for removably clamping a living vessel about a tube during a medical procedure so as to hold the tube within the vessel; said clip comprising:
   (a) a pair of opposed jaws having curved opposed faces adapted to surround the vessel when together; each of said faces generally being C-shaped;
   (b) a pair of arms; each of said arms connected to respective first ends of said jaws;
   (c) said arms being joined near an end thereof opposite connection of said arms to said jaws by a maleable and generally non-resilient hinge; said hinge being deformable upon application of opposed pressure to said jaws such that the angular spacing between said arms and jaws is varied by said application of pressure and a resulting configuration is retained after removal of the pressure such that when pressure is applied to said jaws to bias said jaws together both opposed first ends of said jaws are urged into touching relationship and said jaw surfaces define an opening therebetween adapted to surround the vessel, while said hinge holds said jaw ends in the touching relationship;
   (d) at least a first of said arms being bent medially therealong outwardly with respect to the second of said arms; and
   (e) said first arm being sufficiently pliable whereat said first arm is bent to allow said first arm to be at least partially unbent when pressure is applied thereto; said jaw first ends attached to said arms functioning as a fulcrum when in touching relationship such that when pressure is applied to said first arm whereat said first arm is bent in a direction toward said second arm, said jaws pivot about said fulcrum such that said jaw ends opposite said fulcrum become spaced apart so as to allow release of said clip from the vessel.

2. The clip according to claim 1 wherein:
   (a) both of said arms are bent outwardly with respect to one another prior to use and are maleable so as to be shapeable to become substantially more linear by application of pressure thereto and to retain a more linear shape after pressure is removed therefrom.

3. The clip according to claim 1 wherein:
   (a) said jaws are C-shaped in cross-section and generally encircle a cylindrical volume therebetween when abutting one another at opposite ends thereof.

4. The apparatus according to claim 1 including:
   (a) a tool for applying and removing said clip; said tool including opposed third and fourth jaws and pliers-like means to be operated by a user to selectively bias said third and fourth jaws together and apart;

(b) said third and fourth jaws having surfaces thereon mateable in first and second configurations with said clip such that in said first configuration when said third and fourth jaws are compressed said clip jaws are urged together into generally abutting relationship on both sides thereof and in said second configuration, when said third and fourth jaws are compressed, said first arm is substantially unbent so as to allow said first jaw to pivot about said fulcrum such that sides of said clip jaws not attached to said arms become substantially spaced.

* * * * *